United States Patent [19]
Lafferty et al.

[11] Patent Number: 4,786,598
[45] Date of Patent: Nov. 22, 1988

[54] PROCESS FOR THE BIOTECHNOLOGICAL PREPARATION OF POLY-D-(−)-3-HYDROXYBUTYRIC ACID

[75] Inventors: Robert M. Lafferty; Gerhart Braunegg, both of Graz, Austria

[73] Assignee: Petrochemie Danubia Ges.m.b.H., Mannsworth, Austria

[21] Appl. No.: 675,969

[22] Filed: Nov. 23, 1984

[30] Foreign Application Priority Data

Dec. 1, 1983 [DE] Fed. Rep. of Germany ....... 3343551

[51] Int. Cl.$^4$ .......................... C12P 7/42; C12R 1/05
[52] U.S. Cl. .................................... 435/146; 435/829
[58] Field of Search ....................... 435/146, 253, 829

[56] References Cited

U.S. PATENT DOCUMENTS

4,138,291  2/1979  Lafferty ............................. 435/253

FOREIGN PATENT DOCUMENTS

015669  9/1980  European Pat. Off. ............ 435/146
046344  2/1982  European Pat. Off. ............ 435/146

OTHER PUBLICATIONS

Nur, Israel et al., *Journal of General Microbiology*, vol. 128; 1982; pp. 2937-2943.

Malik et al.; "Nitrogen Fixation by the Hydrogen-Oxidizing Bacterium *Alcaligenes latus*"; *Arch. Microbiol.*, vol. 129, (1981); pp. 254-256.

*Primary Examiner*—Elizabeth C. Weimar
*Attorney, Agent, or Firm*—Mark Dryer

[57] ABSTRACT

The present invention relates to a process for the biotechnological preparation of poly-D-(−)-3-hydroxybutyric acid (PHB) which comprises continuously culturing a microorganism that is a strain of Alcaligenes latus or a PHB-producing mutant thereof, in two separate successive fermentation stages with unrestricted supply of nutrients. The PHB-containing microorganism population cultured in the first stage with a dissolved oxygen content of 25 to 50% of the saturation value for air is then continuously transferred into a second fermentation stage in which the culture is continued at a dissolved oxygen content of 8–15% of the saturation value of air. The PHB is extracted in the usual manner from the biomass thereby obtained.

13 Claims, No Drawings

PROCESS FOR THE BIOTECHNOLOGICAL PREPARATION OF POLY-D-(—)-3-HYDROXYBUTYRIC ACID

The present invention relates to a process for the biotechnological preparation of poly-D-(—)-3-hydroxybutyric acid, herein after referred to as PHB, with a high yield coefficient and an improved enrichment of PHB in the bacterial cell material, in which a microorganism is cultured continuously in two separate, successive fermentation stages.

It has been known for a relatively long time that a large number of microorganisms of procaryotic nature are capable of accumulating PHB as a stored substance for energy and carbon inside their cells. The PHB isolated from the cell material of the microorganism is a thermoplastic polyester with advantageous physical properties which suggest that it can be used for purposes similar to those for which, for example, polyethylene or polystyrene are at present available. Compared with these polymers which are customary today, however, PHB has the advantage that it is accessible via a biotechnological route and can also be degraded again by a biological route.

It is also already known that aerobic culturing of PHB-storing microorganisms can be preferentially controlled in the direction of cell division and growth or in the direction of PHB storage inside the cells by the specific composition of the nutrient medium. In the known processes, enrichment of PHB in the cells of the microorganism is achieved if the concentration of the carbon source in the nutrient medium is high in relation to the supply of other nutrients required for growth, for example nitrogen and phosphorus, and the microorganism is cultured, for example, under ammonium-limited growth conditions.

A two-stage process for the preparation of PHB which is based on this knowledge is described, for example, in European Patent No. A-15,669. In this process, a microorganism of the genus *Methylobacterium organophilium* is first cultured with an unrestricted supply of nutrients, including a complete and adequate supply of nitrogen and phosphorus, until the microorganism population has reached a concentration of, preferably, 20 to 25 g of biomass per liter of culture liquid, without accumulation of PHB inside the cells occurring in this growth phase. Complete interruption of the nitrogen and/or phosphorus supply of the culture medium in the second fermentation stage then causes a stop in reproduction and bacterial growth, accumulation of PHB inside the cells first occurring in this phase. According to the statements of European Patent No. A-15,669, biomasses with a PHB content of at most 25 to 7% by weight of the cell dry weight are obtained in this process.

A fermentation process for the preparation of PHB which is improved in respect of the above process is described in European Patent No. A-46,344, this process being based on continuous aerobic culturing of microorganisms of the species *Alcaligenes eutrophus*. According to the statements made in that publication, it is possible in this process to achieve controlled growth of the microorganism population and at the same time enrichment of PHB inside the cells by restricting, in contrast to the process of European Patent No. A-15,669, the supply of the nutrients and trace substances essential for growth, in particular the supply of nitrogen, from the start of culturing.

In a process variant which is also envisaged, the culture liquid which contains the microorganism and which is initially already enriched to 25% by weight of PHB under limited nutrient supply, is transferred to a second fermentation stage and enriched there to 50 to 80% by weight of PHB, those nutrient components of which the concentration has already been limited in the first stage to suppress growth being no longer added at all in the second stage to the nutrient solution, since growth is no longer desirable at all during the accumulation phase.

Although better utilization of the carbon source in the nutrient medium and an improved accumulation of the PHB is achieved with the process of European Patent No. A-46,344, it proves to be a disadvantage that both the specific growth rate and the PHB-formation rate are significantly reduced by the deficient supply of nutrients essential for growth.

Another disadvantage of this process is that with the species *Alcaligenes eutrophus*, the optimum temperature range for fermentation is relatively low. The microorganism must therefore be cultured with severe cooling at 30 to 34° C. in a temperature range in which both the growth and the accumulation of PHB proceed more slowly than in the case of microorganisms with a higher thermotolerance, which can be cultured at a higher temperature.

For the reasons mentioned, the profitability of the preparation of PHB in the known processes is adversely affected by the long residence times and the correspondingly low dilution rates during continuous operation of the fermenter.

Of the carbohydrates, the source of carbon in the process of European Patent No. A-46,344 is above all fructose, and only in the case where particular mutants derived from the strain *Alcaligenes eutrophus* H 16 are employed can a deviation be made to glucose as the nutrient source. Apart from the fact that culture and harvesting of the mutants from the parent strain is labor-intensive, the amount of utilizable nutrient sources, which would enable economical preparation of PHB, which can be obtained by using these mutants is not substantially increased, since the large amounts of disaccharides which are available and serve as a main supply of glucose, for example the sucrose contained in molasses or industrial sugar solutions, also cannot be utilized for the mutants derived from *Alcaligenes eutrophus* H 16.

Although other species of the genus Alcaligenes, besides *Alcaligenes eutrophus*, are mentioned in European Patent No. A-46,344 as being useful for accumulation of PHB, for example *Alc. faecalis, Alc. ruhlandii, Alc. latus* and *Alc. aquamarinus*, further details of the culture and enrichment conditions are not given for any of these species and the procedure of the invention is disclosed in the description and in the examples only for strains of *Alcaligenes eutrophus*.

In contrast, the object of this invention is to provide a more economical two-stage process for the continuous fermentative preparation of PHB with a high yield coefficient and an improved enrichment of PHB in the cell material of the microorganism utilizing cheaper sources of carbon, in which the disadvantages of the known processes are avoided.

In achieving this object, it has now been found, surprisingly, that a very rapid growth of the microorganism population with simultaneous effective PHB accumulation can be achieved at a high dilution rate and that the dependency of the microorganism on the nature of the utilizable carbon source can be largely eliminated if strains of *Alcaligenes latus* or mutants thereof are cultured in the temperature range from 36 to 42° C. in a two-stage fermentation process under conditions which were not hitherto known for the fermentative preparation of PHB.

Some of the essential features of this new improved production process for PHB are that, in contrast to the known prior art, the reproduction and rapid growth of the microorganism population is promoted by an unrestricted supply of nutrients, including a complete and adequate supply of nitrogen and phosphorus, and, surprisingly, at the same time an effective intracellular accumulation of PHB is achieved, without the culture being subjected to growth-limiting conditions.

It has been found that under these conditions preparation of PHB can be carried out in a particularly productive manner and a good utilization of the carbon source in the nutrient medium can be achieved if the microorganism is cultured continuously in two separate, successive culture stages with unrestricted supply of nutrients, but culture in the second stage is continued at a lower dissolved oxygen content in the nutrient medium than in the first stage.

In this manner, biomasses with a significantly better enrichment of PHB than that corresponding to the prior art are formed in the fermenter within shorter residence times, the preparation and isolation of the PHB taking place in a more economical manner than was hitherto possible.

The present invention accordingly relates to a process for the preparation of poly-(D)-(−)-3-hydroxybutyric acid which comprises continuously culturing a strain of the microorganism *Alcaligenes latus* or a PHB-producing mutant derived from this microorganism under aerobic conditions in an aqueous culture medium containing sources of assimilable carbon, nitrogen and phosphorus and the supply of trace nutrients required for the growth of said microorganism with a complete supply of nutrients which is optimum for the growth of the microorganism, under unlimited growth conditions in the temperature range from 36° to 42° C. in two separate successive fermentation stages comprising a first fermenter and a second fermenter under sterile conditions, the PHB-containing microorganism population cultured in the first fermenter with a dissolved oxygen content of 25 to 50% of the saturation value for air being continuously transferred, together with the culture solution, into the second fermenter in which the culture is continued at a dissolved oxygen content of 8–15% of the saturation value for air, and isolating the PHB by extraction from the biomass thereby obtained.

All the known strains of *Alcaligenes latus* are suitable for carrying out the process. Preferred bacterial strains in the process of the invention are strains of *Alcaligenes latus* selected from the group consisting of *Alcaligenes latus* DSM No. 1122, DSM No. 1123 and DSM No. 1124.

The morphological properties of these strains are described in the literature by Palleroni et al. in Int. Journ. of Systematic Bacteriology 28, 416–428, 1978, and recorded in catalogues of culture collections, for example in the American Type Culture Collection (ATCC). Culture samples of the microorganisms identified by DSM numbers are freely obtainable to the expert from the Deutsche Sammlung für Mikroorganismen [German Collection of Microorganisms] in Göttingen of the Gesellschaft für biotechnologische Forschung [Biotechnological Research Association], MBH in Stockheim, Federal Republic of Germany.

The PHB-accumulating mutants of strains of *Alcaligenes latus* which have been obtained from the parent strains by customary processes are also suitable for carrying out the process according to the invention.

Strains of *Alcaligenes latus* have the property, which is advantageous for economical PHB production, that they are capable of utilizing a wide range of carbon sources for growth and for PHB accumulation. Examples which may be mentioned of carbon sources are carbohydrates, such as D-glucose, D-fructose, lactose, maltose, sucrose, starch, molasses, betaine, green syrup, hydrol and cellulose hydrolysates; organic acids and their esters and salts, such as water-soluble salts of gluconic, 2-ketogluconic, formic, acetic, butyric, isobutyric, L-malonic, D-(−)-tartaric, aconitic, itaconic, m-hydroxybenzoic, p-hydroxybenzoic, gentisic, protocatechuic and mandelic acid; alcohols, such as n-propanol, isopropanol, 2,3-butylene glycol, propylene glycol and glycerol; aminoacids, such as β-alanine, L-alanine, L-serine, L-threonine, L-leucine, L-citrulline, L-ornithine, L-aminobutyrate, L-aspartate, L-asparagine, L-glutamate, L-proline, hippurate, sarcosine and creatine; or amines, such as butylamine.

In accordance with their properties as optionally chemolithoautotrophic microorganisms, the strains of *Alcaligenes latus* are, however, also capable of utilizing carbon dioxide, in addition to the carbon sources so far listed, if the carbon dioxide is available in a mixture together with hydrogen and oxygen as the sole carbon source.

Since the profitability of a biotechnological process for the preparation of PHB very largely depends on the cost of the carbon source in the nutrient substrate, the fact that such a large number of compounds can be used in the fermentation process according to the invention is of great advantage, since the process can be modified for the particular cheapest carbon source.

The excellent utilizability of the readily accessible disaccharides is a surprising and advantageous feature of the process according to the invention, taking into consideration the availability of the nutrient substrate and the profitability of the PHB preparation. In a preferred embodiment, sucrose, which is contained in industrial sugar solutions, for example green syrup, or in waste products of the production of sugar, for example beet molasses, is presented to the microorganism as the source of carbon, culture of the strain *Alcaligenes latus* DSM No. 1123 with sucrose again being particularly advantageous because of the high rate of PHB product formation. If the assimilable carbon compounds presented to the microorganism are those from the group which at the same time contain nitrogen in the molecule, the carbon and nitrogen requirement can be met from the same source. Ammonia, ammonium salts, for example ammonium chloride or ammonium sulfate, and nitrates are also utilized by the *Alcaligenes latus* strains as a nitrogen source. The nitrogen requirement necessary can furthermore also be largely met by the nitrogen content of industrial and biological effluents.

The composition of the nutrient solution with respect to its other mineral components includes phosphorus, for example in the form of sodium hydrogen phosphate or potassium hydrogen phosphate, magnesium, for example as magnesium sulfate, calcium, for example as calcium chloride, and iron, for example in the form of iron-III chloride, iron sulfate or iron-III ammonium citrate. Other trace minerals which are essential for growth can preferably be added to the nutrient medium in the form of a trace solution which has, for example, the following composition:

$ZnSO_4.7H_2O$—100 mg/l
$Ml_2.4H_2O$—30 mg/l
$H_3BO_3$ 300 mg/l
$CoCl_2.6H_2O$—200 mg/l
$CuSO_4.5H_2O$—10 mg/l
$NiCl_2.6H_2O$—20 mg/l
$NaMoO_4.2H_2O$—30 mg/l

In carrying out the process according to the invention, a procedure is advantageously followed in which one or more precultures are first prepared, for example in a liquid nutrient medium, and a nutrient solution of the given composition which has been prepared in a production fermenter is inoculated with the well-grown preculture in a ratio of about 1:5 to 1:15.

During the entire duration of culturing, care is taken in both stages of the fermentation, by supplementing the nutrient substrates consumed, that the sources of carbon, nitrogen and phosphorus and of all the organic and inorganic trace nutrients are kept within the concentration optimum for bacterial growth. Optimum nutrient supply in the context of the present invention is to be understood as meaning culture of the microorganism in a culture medium which, throughout the entire duration of the fermentation, contains all the components of the complete nutrient supply in concentrations such that unlimited growth conditions prevail in the culture and the microorganism experiences no deficiency and no limitation in the supply of nutrients which are essential for growth, for example nitrogen or phosphorus.

The optimum supply of nitrogen for bacterial growth is determined by the method of Warburg, described in Manometric Techniques by Umbreit W. W., Burris R. H., Stauffer J. S., Burges Publishing Company, Minneapolis, USA, 1964, using a Warburg respirator. For strains of *Alcaligenes latus*, the optimum nitrogen supply, without providing limiting conditions for growth, as a rule exists when a concentration of at least 200 mg of ammonium sulfate per liter of culture liquid, corresponding to a nitrogen concentration of at least 45 mg/l, is present in the culture medium throughout the entire fermentation, a nitrogen concentration of about 50 to 320 mg/l being in turn particularly preferred in the first fermentation stage.

For optimum phosphorus supply, a concentration of at least 500 mg/l of phosphorus is recommended, and it is in turn particularly preferable to maintain a concentration of 600 mg to 1.2 g/l.

A nutrient solution which is optimum for the process contains, for example, from 1.5 to 40 g of sucrose per liter of the culture medium as the carbon source, a concentration of 4 to 10 g/l of sucrose being particularly preferred in the first fermentation stage. Surprisingly, in the culture of strains of *Alcaligenes latus* under the conditions according to the invention, no pronounced accumulation phase for PHB appears as a function of the nutrient limitation, for example by deficient supply with nitrogen, but an extremely efficient PHB enrichment associated with the growth is to be observed under favorable growth conditions for the microorganism, with complete nutrient supply.

The growth-associated PHB accumulation with unrestricted nutrient supply has the advantage that neither the specific growth rates nor the PHB product formation rates are reduced by nutrient deficiency, and therefore a higher concentration of biomass with a better PHB enrichment is obtained within considerably shorter fermentation times than in the case of the known processes which operate with limited nutrient supply.

On the basis of these high growth and product formation rates, dilution rates D of, for example, 0.3 hour$^{-1}$ to 0.41 hour$^{-1}$ are achieved in the first fermentation stage of the process according to the invention, at a PHB accumulation of more than 70% by weight of the cell dry weight, and in the second stage dilution rates of 0.28 hour$^{-1}$ to 0.33 hour$^{-1}$ are even achieved.

(The dilution rate $D = \dfrac{F \text{ feed or discharge of the fermenter in liters per hour}}{V \text{ operating volume of the fermenter in liters}}$, and has the dimension $|\text{hour}^{-1}|$).

In the first fermentation stage, the nutrient solution is advantageously introduced into the fermenter, which is preferably a fermentation kettle, in a continuous feed process until the maximum operating volume of the fermenter is reached. When the maximum operating volume is reached, the process is further carried out continuously by adding to the culture, on the one hand, a constant stream of fresh nutrient solution and, on the other hand, removing from the fermenter an amount of nutrient solution, equivalent to the feed, containing the PHB-containing microorganism population formed and transferring this amount to the second fermenter Culture is effected under aerobic conditions, for example with the supply of oxygen or air, the dissolved oxygen content advantageously being maintained in a range from 25 to 50% of the saturation value for air in the first stage by varying the amount of air or oxygen introduced per unit time. To promote unimpeded growth and PHB enrichment, it is advantageous to introduce sterile air into the stirred culture medium. It is also possible to keep the dissolved oxygen content within the desired range by varying the stirrer speed.

The dilution rates under the given conditions are advantageously chosen such that, after reaching a stable equilibrium condition, the microorganism population in the first fermenter is kept at a concentration of about 15 to 25 g of bacterial dry mass per liter of culture liquid at a PHB content of at least 60% by weight of the cell dry weight, a PHB content of at least 70% by weight in turn being particularly advantageous for an economical procedure for the process.

The second fermenter can have the same shape as the first, and be designed as a stirred kettle. Since the dilution rate in the second fermentation stage is as a rule lower than that in the first stage, to maintain continuous operation, the culture of the microorganism in the second stage must be continued in a larger fermenter, the operating volume of which is such that account is taken of the different dilution rates in the first and second stage and the additional nutrient feed.

The residual concentration of nutrients contained in the feed from the first fermenter is continuously supplemented by addition of fresh nutrients to the extent such that optimum and complete nutrient supply is also ensured in the second stage. This measure means that the growth phase is maintained throughout the entire duration of the fermentation and accumulation of the PHB within the cells is effected in a growth-associated manner, at a high rate. In addition, a relative increase in the accumulating cells is to be observed in the second fermentation stage under growth conditions, so that removal of the biomass from the nutrient solution is easier to carry out. The cell masses can thereby usually be separated off well, for example by simple filtration, and more expensive devices, for example the provision of centrifuges for the separation operation, can be spared.

Since the point in time of maximum exponential growth of the microorganism population has already been passed in the second fermentation stage, it may be advantageous to keep the nutrient concentrations at the lower limit of the ranges stated above for optimum nutrient supply, in order to achieve the best possible utilization of the nutrients employed.

The composition of the nutrient medium and the feed of fresh nutrients in the second fermentation stage are therefore advantageously regulated such that the concentration of the carbon source in the culture liquid does not fall below the value of about 1.5 g of sucrose per liter of culture liquid, a concentration of 1.5 g to 2.5 g again being particularly preferred. The nitrogen concentration is at least 45 mg, but is preferably about 50 to 60 mg, per liter of culture liquid.

The dissolved oxygen content of the nutrient solution is reduced to 8-15%, preferably to 8-10%, of the saturation value for air in the second fermentation stage. The reduction in the dissolved nutrient content has the advantage that, on the one hand, the costs for oxygen transfer are reduced, and at the same time the carbon source in the nutrient medium can be better utilized. Better utilization of the nutrient source is of particular importance because the residual concentration of carbon in the discharge after the end of the fermentation can thereby be substantially reduced.

Under the conditions of the process according to the invention, the microorganism is capable of enriching the PHB content in the cells up to about 84% by weight of the cell dry weight. When the process is carried out in practice, the dilution rate in the second fermentation stage is advantageously adjusted such that the microorganism population is enriched to a concentration of 15-35 g of cell dry weight per liter of culture liquid at a PHB content of 70-80% by weight, preferably 75-80% by weight, of the cell dry weight.

In contrast to the species *Alcaligenes eutrophus*, the strains of *Alcaligenes latus* are surprisingly more thermotolerant. This increased thermotolerance is manifested by the fact that the optimum temperature range for fermentation is 36° to 42° C. in both stages, a temperature of 37° to 39° C. in turn being preferred. Besides the accelerating effect on growth and PHB accumulation, culture in this temperature range has the advantage that the cooling costs can be considerably reduced during fermentation. The saving in cooling costs by culture at a higher temperature together with shorter residence times is of particular importance, since the cooling costs as a rule make up half of the energy costs which arise during operation of a fermenter.

Throughout the entire duration of the fermentation, the pH value of the nutrient solution is advantageously adjusted to values between 6.5 and 7.5, preferably to values from 6.8 to 7.2, by continuous addition of buffer solution, for example phosphate buffer solution, or aqueous base, for example potassium hydroxide solution or sodium hydroxide solution.

Under the stated conditions, continuous operation of the process can be maintained for weeks without changes resulting in the composition of the biomass obtained or in the yield coefficient.

If carbohydrates are used as the carbon source, yield coefficients $Y_{x/s}$ of 0.42 to 0.46 are achieved in both process stages of the process according to the invention, that is to say 0.42 to 0.46 g of cell dry weight in the form of PHB-containing biomass is obtained per gram of carbohydrate employed.

Culture solution containing the PHB-enriched microorganism population is removed at a rate corresponding to the feed into the second fermenter, and the cell masses are separated off by customary separation methods, such as decanting or centrifuging, but preferabl by filteration, and the PHB is isolated therefrom by extraction in the customary manner, for example by the process of U.S. Pat. No. 4,101,533.

The nutrient solution freed from the biomass as a rule now contains only low nutrient concentrations.

To utilize the remaining nutrients, the nutrient solution which has been freed from cells can be recycled to the first fermenter, fresh nutrient solution being added to achieve the optimum nutrient concentration and used for further cultures.

The invention is illustrated in more detail in the following example:

EXAMPLE 10 liters of a nutrient medium I containing 1.5 g/l of $(NH_4)_2SO_4$ and 15 g/l of sucrose are introduced, in sterile-filtered form, into a sterile fermenter with an operating volume of 15 liters and are inoculated with 1 l of a well-grown preculture of *Alcaligenes latus* DSM No. 1123.

The medium I has the following composition:
$Na_2HPO_4.2H_2O$: 4.5 g/l
$KH_2PO_4$: 1.5 g/l
$MgSO_4.7H_2O$: 0.2 g/l
$CaCl_2.2H_2O$: 0.02 g/l trace solution: 2 ml/l
Fe-III $NH_4$citrate: 0.05 g/l
The trace solution has the following composition:
$ZuSO_4.7H_2O$: 100 mg/l
$MnCl_2.4H_2O$: 30 mg/l
$H_3BO_3$: 300 mg/l
$CoCl_2.6H_2O$: 200 mg/l
$CuCO_4.5H_2O$: 10 mg/l
$NiCl_2.6H_2O$: 2.0 mg/l
$NaMoO_4.2H_2O$: 30 mg/l The dissolved oxygen content is kept between 28 and 30% of the saturation value for air by varying the stirrer speed and the aeration rate, and the operating temperature is 37° C. During the fermentation, the pH value of the nutrient solution is kept constant at 7.0 by automatic titration with a 10% strength sterile aqueous NaOH solution.

In the further course of the culture, the nutrient substrates are kept constant by means of a continuous feed method by a feed with fresh nutrient solutions adapted to the consumption rates and the dilution. The fresh nutrient solutions consist of sucrose solution with a concentration of 300 g/l $(NH_4)_2SO_4$ solution with a concentration of 200 g/land fresh medium I.

When the maximum operating volume of the reactor has been reached, a continuous procedure is set up such that a constant stream of fresh nutrient solution is fed to the culture on the one hand, and on the other hand an amount of nutrient solution equivalent to the flow is removed and transferred in a continuous stream to a second fermenter with an operating volume of 25 l. The nutrient solution freshly fed in contains sucrose in a concentration of 40 g/l (NH$_4$)$_2$SO$_4$ in a concentration of 4.6 g/l and fresh medium I in the abovementioned composition. In this manner, a stable equilibrium condition is achieved after some time, the culture broth in the first fermentation stage containing 16.5 g/l of dry biomass with a PHB content of 71% by weight.

The overflow to the second fermenter still contains a residual concentration of (NH$_4$)$_2$SO$_4$ of 0.45 g/l and a residual concentration of sucrose of about 4.1 g/l. In the equilibrium state, 6.0/hour of fresh nutrient medium are fed in, corresponding to a dilution rate of D=0.4 hour$^{-1}$.

In the second fermenter, which has a maximum operating volume of 25 l, the temperature and pH value are established and kept constant as in the first fermentation stage. In contrast, the dissolved oxygen concentration is reduced to 8–10% of the saturation value for air by varying the aeration rate and stirrer speed. In addition to the feed from the first fermentation stage, the second fermenter is also supplied with 1.5 l per hour of a sterile aqueous nutrient solution containing 26.64 g/l of ammonium sulfate and sucrose with a concentration of 236 g/l, so that the concentration of these two substrates also does not become limiting in this phase. By these measures, the growth phase is maintained throughout the entire culture operation.

Under these conditions, a culture broth containing 35.5 g per liter of dry biomass with a constant PHB content of 79% by weight is obtained in the discharge of the second fermentation stage. A dilution rate of D=0.30 hour$^{-1}$ results in this second stage, corresponding to an overall flow of 7.5 l per hour.

This continuous fermentation can be maintained without problems for a period of three weeks without any changes resulting in respect of the yield coefficient $Y_{x/s}=0.46$ or in the composition of the biomass.

The operating conditions for the continuous two-stage preparation of PHB with *Alcaligenes latus* strain DSM No. 1123 are summarized in the following Table I.

TABLE I

|  | Stage 1 | Stage 2 |
|---|---|---|
| Operating volume | 15 l | 25 l |
| Stirring | crosswise blade | crosswise blade |
| Temperature | 37° C. | 37° C. |
| pH value | 7.0 | 7.0 |
| O$_2$ concentration (% of air saturation) | 28–30% | 8–10% |
| Dilution rate D | 0.4 hour$^{-1}$ | 0.3 hour$^{-1}$ |
| Carbon source | sucrose | sucrose |
| Sucrose concentration in the feed | 40 g/l | — |
| Nitrogen source | (NH$_4$)$_2$SO$_4$ | (NH$_4$)$_2$SO$_4$ |
| Concentration of (NH$_4$)$_2$SO$_4$ in the feed | 4.6 g/l | — |
| Residual concentration of sucrose | 4.1 g/l | 2.1 g/l |
| Residual concentration of (NH$_4$)$_2$SO$_4$ | 0.45 g/l | 0.085 g/l |
| Sucrose consumption | 35.9 g/l | — |
| (NH$_4$)$_2$SO$_4$ consumption | 4.15 g/l | — |
| Biomass concentration | 16.5 g/l | 35.5 g/l |
| PHB content of the biomass | 71% of the cell dry weight | 79% |
| Biomass productivity | 99 g/hour | 266.4 g/hour |
| PHB productivity | 70.4 g/hour | 210.46 g/hour |
| $Y_x$, sucrose | 0.46 g/g | 0.46 g/g |
| $Y_x$, (NH$_4$)$_2$SO$_4$ | 3.98 g/g | 3.98 g/g |
| (NH$_4$)$_2$SO$_4$ concentration in the part stream of fermenter 2 | — | 26.64 g/ (1.5 l/hour) |
| Sucrose concentration in the part stream of fermenter 2 | — | 236 g/l (1.5 l/hour) |
| Biomass concentration in the feed |  | 13.2 g/l |

What we claim is:

1. Process for the preparation of poly-(D)-(−)-3-hydroxybutric acid, hereinafter referred to as PHB, which comprises continuously culturing a strain of the microorganism *Alcaligenes latus* or a PHB-producing mutant derived from this microorganism under aerobic conditions in an aqueous culture medium containing sources of assimilable carbon, nitrogen and phosphorus and the supply of trace nutrients required for the growth of said microorganism with a complete supply of nutrients which is optimum for the growth of the microorganism, under unlimited growth conditions in the temperature range from 36° to 42° in two separate successive fermentation stages comprising a first fermenter and a second fermenter under sterile conditions, the PHB-containing microorganism population cultured in the first fermenter with a dissolved oxygen content of 25 to 50% of the saturation value for air being continuously transferred, together with the culture solution, into the second fermenter in which the culture is continued at a dissolved oxygen content of 8–15% of the saturation value for air, and isolating the PHB by extraction from the biomass thereby obtained.

2. Process according to claim 1 in which the strain of *Alcaligenes latus* is selected from the group consisting of *Alcaligenes latus* DSM No. 1122, DSM No. 1123 and DSM No. 1124.

3. Process according to claim 1 in which sucrose is used as the source of carbon.

4. Process according to claim 3 in which the strain *Alcaligenes latus* DSM No 1123 is cultured.

5. Process according to claim 3 in which the entire culturing is carried out in a nutrient medium containing 1.5 to 40 g of sucrose, as the source of carbon per liter of culture liquid.

6. Process according to claim 1 in which the culturing is carried out in a nutrient medium which contains at least 45 mg of nitrogen per liter of culture liquid throughout the entire duration of the fermentation.

7. Process according to claim 1 in which the culturing is carried out in a nutrient medium containing, per liter of culture liquid, 4 to 10 g of sucrose, as the source of carbon, and 50 to 320 mg of nitrogen in the first fermentation state and 1.5 to 2.5 g of sucrose, as the source of carbon, and 50 to 60 mg of nitrogen in the second fermentation stage.

8. Process according to claim 1 in which the entire culturing is carried out in a nutrient medium containing 600 mg to 1.2 g of phosphorus per liter of culture liquid.

9. Process according to claim 1 in which the microorganism is cultured in the first fermentation stage to give a concentration of 15 to 25 g of bacterial dry mass per liter of culture liquid at a PHB content of at least 70% by weight.

10. Process according to claim 1 in which the culturing in the second fermentation stage is carried out at a dissolved oxygen content of 8–10% of the saturation value for air.

11. Process according to claim 1 in which the PHB content of the biomass is enriched to 75–80% by weight of the cell dry weight in the second fermentation stage.

12. Process according to claim 1 in which the entire culturing is carried out at 37° to 39° C.

13. Process according to claim 1 in which the entire culturing is carried out at a pH value of 6.8 to 7.2.

* * * * *